United States Patent [19]
Smyth

[11] Patent Number: 5,866,699
[45] Date of Patent: Feb. 2, 1999

[54] OLIGONUCLEOTIDES WITH ANTI-MDR-1 GENE ACTIVITY

[75] Inventor: Adrienne P. Smyth, Charlton, Mass.

[73] Assignee: Hybridon, Inc., Cambridge, Mass.

[21] Appl. No.: 276,567

[22] Filed: Jul. 18, 1994

[51] Int. Cl.$^6$ ............... C07H 21/04; A61K 48/00
[52] U.S. Cl. ............... 536/24.5; 536/23.1; 514/44; 935/8
[58] Field of Search ............... 514/44; 536/23.1, 536/23.5, 24.31, 24.5; 935/34

[56] References Cited

U.S. PATENT DOCUMENTS

| | | | |
|---|---|---|---|
| 5,149,798 | 9/1992 | Agrawal et al. | 536/27 |
| 5,198,344 | 3/1993 | Croop et al. | 435/69.1 |
| 5,206,352 | 4/1993 | Roninson et al. | 536/24.31 |
| 5,225,326 | 7/1993 | Bresser et al. | 435/6 |
| 5,314,801 | 5/1994 | Nycz et al. | 435/6 |

FOREIGN PATENT DOCUMENTS

| | | |
|---|---|---|
| WO 92/14467 | 9/1992 | WIPO . |
| WO 93/19094 | 9/1993 | WIPO . |
| WO 93/24613 | 12/1993 | WIPO . |
| WO 94/06938 | 3/1994 | WIPO . |
| WO 95/10938 | 4/1995 | WIPO . |

OTHER PUBLICATIONS

K Ueda et al (1987) J Biol Chem 262:505–508.
R Weiss (1991) Science News 139: 108–109.
CA Stein et al (1993) Science 261: 1004–1012.
JF Milligan et al (1993) J Med Chem 36: 1923–1937.
P Westermann et al (1989) Biomed Biochim Acta 48: 85–93.
N Miller et al (1994) Parasitology Today 10: 92–97.
RA Stull et al (1995) Pharmaceutical Research 12: 465–483.
S Wu–Pong (1994) Pharmaceutical Technology 118: 102–114.
RW Wagner (1994) Nature 372: 333–335.
CD Bucana et al (1993) J Histochem Cytochem 41: 499–506.
Zamecnik et al. (1978) *Proc. Natl. Acad. Sci.* (USA) 75:280–284.
Tsuruo et al. (1981) *Cancer Res.* 41:1967–1972.
Froehler (1986) *Tetrahedron Lett.* 27:5575–5578.
Carmichael et al. (1987) *Cancer Res.* 47:936–942.
Ozols et al. (1987) *J. Clin. Onc.* 5:641–647.
Ueda et al. (1987) *Proc. Natl. Acad. Sci.* (USA) 84:3004–3008.
Agrawal et al. (1987) *Tetrahedron Lett.* 28:(31):3539–3542.
Caruthers et al. (1987) *Meth. Enzymol.* 154:287–313.
Pastan et al. (1988) *Proc. Natl. Acad. Sci.* (USA) 85:4486–4490.
Agrawal et al. (1988) *Proc. Natl. Acad. Sci.* (USA) 85:7079–7083.
Rotman et al. (1988) *In Vitro Cell. Develop. Biol.* 24:1137–1146.
Kessel (1989) *Cancer Commun.* 1:145–149.
Kioka et al. (1989) *Biochem. Biophys. Res. Comm.* 162:224–231.
Vasanthakumar et al. (1989) *Cancer Commun.* 1:225–232.
Chen et al. (1990) *J. Biol. Chem.* 265:506–514.
Eliason et al. (1990) *Int. J. Cancer* 46:113–117.
Jaroszewski et al. (1990) *Cancer Commn.* 2:287–294.
Kane et al. (1990) *J. Bioenerg. Biomemb.* :593–618.
Rivoltini et al. (1990) *Int. J. Cancer* 46:727–732.

(List continued on next page.)

*Primary Examiner*—Bruce R. Campell
*Attorney, Agent, or Firm*—Hale and Dorr LLP

[57] ABSTRACT

Disclosed are synthetic oligonucleotides having a nucleotide sequence complementary to at least a portion of the multidrug resistant-1 gene, or transcripts thereof, which portion encodes a nucleoside binding site. Also disclosed is a pharmaceutical formulation containing such oligonucleotides, and methods of treating multidrug resistant cancer cells, of preventing the expression of P170 in a cell, and of preventing the induction of multidrug resistance in a cancer cell.

4 Claims, 7 Drawing Sheets

OTHER PUBLICATIONS

Uhlmann et al. (1990) *Chem. Rev.* 90:543–584.
Kessel et al. (1991) *Cancer Res.* 51:4665–4670.
Meitner (1991) *Oncology* 5:75–88.
Bruggeman et al. (1992) *J. Biol. Chem.* 267:21020–21026.
Clynes et al. (1992) *Cytotechnology* 10:75–89.
Corrias et al. (1992) *Anticancer Res.* 12:1431–1438.
Valverde et al. (1992) *Nature* 355:830–833.
Agrawal et al. (1992) *Trends Biotechnol.* 10:152–158.
Bergot et al. (1992) *J. Chromatog.* 559:35–42.
Attia–Sobol et al. (1993) *Cancer* 29A:1081–1088.
Efferth et al. (1993) *Oncol.* 50:303–308.
Gottesman (1993) *Cancer Res.* 53:747–754.
Leonce et al. (1993) *Biol. Cell.* 78:63–68.
Redmond et al. (1993) *Cancer* 29A:1078–1081.
Robinson et al. (1993) *Handbook of Flow Cytometry Methods* pp. 191–193.
Thierry et al. (1993) *Biochem. Biophys. Res. Commun.* 190:952–960.
New England Biolabs 1988–1989 Catalog.

OLIGONUCLEOTIDES WITH ANTI-MDR-1 GENE ACTIVITY

BACKGROUND OF THE INVENTION

This invention relates to cancer therapy. More particularly, this invention relates to the modulation of multiple drug resistance in cells by antisense oligonucleotides complementary to portions of the MDR-1 gene.

Chemotherapy has been successfully used to control metastatic cancers which cannot be cured by surgery because of their widespread dissemination throughout the body. However, the effective use of chemotherapy is limited by inherent and acquired resistance of many tumors to a variety of structurally unrelated chemotherapeutic drugs.

One mechanism of drug resistance involves the overexpression of a 170,000 dalton membrane protein, P-glycoprotein (or P170), which acts as an ATP-dependent, chloride-selective efflux pump for a variety of hydrophobic chemotherapeutic drugs (Roninson (1991) *Molecular and Cellular Biology of Multi-Drug Resistance in Tumor Cells,* Plenum Press, NY; Valverde et al. (1992) *Nature* 355: 830–833). This protein is encoded by the multidrug resistance-1 gene (MDR-1) gene. A recent estimate suggests that expression of MDR-1 will result in greater than 250,000 new cancers displaying clinically significant resistance (Gottesman (1993) *Cancer Res.* 53: 747–754).

Reversal or suppression of the resistant phenotype has been accomplished in cell culture systems and in animal experiments with small molecule inhibitors of P170, thereby rendering chemotherapeutic drugs more effective at killing tumor cells (Tsuruo et al. (1981) *Cancer Res.* 41: 1967–1972). For example, verapamil, cyclosporin, and trifluoroperazine have been used to reverse the MDR phenotype (see, e.g., Thierry et al. (1993) *Biochem. Biophys. Res. Commun.* 190: 952–960; and Jaroszewski et al. (1990) *Cancer Commun.* 2: 287–294). However, the clinical use of many of these drugs is limited due to toxic side effects and lack of specificity (see, e.g., Ozols et al. (1987) *J. Clin. Onc.* 5: 641–647).

Immunoglobulins have also been used to modulate P170-mediated drug resistance. For example, it has been demonstrated that monoclonal antibodies and ricin-containing immunotoxins eradicate kidney carcinoma cell cultures (Efferth et al. (1993) *Oncol.* 50: 303–308). However, normal kidney cells expressing high levels of P-170 were similarly affected, indicating that clinical application of these antibodies and immunotoxins may be limited by toxic side effects on normal, P170-expressing tissues in cancer patients.

Recently, new chemotherapeutic agents have been developed which are capable of modulating cellular and foreign gene expression (see, Zamecnik et al. (1978) *Proc. Natl. Acad. Sci.* (USA) 75: 280–284). These agents, called antisense oligonucleotides, bind to target single-stranded nucleic acid molecules according to the Watson-Crick rule or to double stranded nucleic acids by the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Antisense oligonucleotides have been designed to inhibit the expression of MDR-1. For example, oligonucleotides complementary to the initiation codon of MDR-1 have been demonstrated to inhibit P170 expression (Rivoltini et al. (1990) *Int. J. Cancer* 46: 727–732; Vasanthakumar et al. (1989) *Cancer Commun.* 1: 225–232). Oligonucleotides complementary to the 5' end region of MDR-1 have been shown to decrease P170 synthesis and resistance to doxorubicin in various resistant cells (Corrias et al. (1992) *Anticancer Res.* 12: 1431–1438; Thierry et al. (1993) *Biochem. Biophys. Res. Commun.* 190: 952–960), and to inhibit the expression of P170 in kidney carcinoma and normal kidney cells (Efferth et al. (1993) *Oncol.* 50: 303–308). In addition, phosphorothioate oligonucleotides complementary to the 5' end of an intron/exon border, or to an EcoRI site have been demonstrated to inhibit P170 expression, but not necessarily with a decrease in the resistance phenotype.

There is, therefore, a need for better antisense oligonucleotides directed against MDR-1 that provide better diminution of the resistance phenotype.

SUMMARY OF THE INVENTION

The transmembrane protein P-170 protects cells which express this protein from a large group of cytotoxic drugs useful in cancer chemotherapy. This protein has two halves, each of which includes a nucleotide binding region (Chen et al. (1990) *J. Biolog. Chem.* 265: 506–514). These nucleotide binding regions are found in two separate and duplicated internal regions of the multiple drug resistance-1 (MDR-1) gene with shared regions of extensive sequence homology. It has been discovered that oligonucleotides which are complementary to these regions of the MDR-1 gene are able to effectively modulate the expression of P170, and hence, to inhibit multidrug resistance in P-170 expressing cells.

This discovery has been exploited to produce the present invention which provides antisense oligonucleotides that are more effective in inhibiting MDR-1 expression and thereby more effective in diminishing the multiple drug resistance phenotype than other known antisense oligonucleotides directed to MDR-1. Synthetic antisense oligonucleotides according to the invention accomplish this improved effectiveness by binding to two identical sites within the MDR-1 gene or messenger RNA.

The term "MDR-1 gene" as used herein is meant to encompass the human wild type gene which encodes the transmembranous glycoprotein "P-glycoprotein" or "P170," as well as mutated MDR-1 genes and analogs thereof which encode isoforms and analogs of P170 (see, e.g., PCT/US93/04707). The oligonucleotides of the invention hybridize to the MDR-1 gene or transcript thereof under normal physiological conditions existing within a cell expressing MDR-1, and under stringent conditions in vitro.

As used herein, the term "synthetic oligonucleotide" includes chemically synthesized polymers of eight or up to 100, and preferably from about 12 to about 50 ribonucleotide and/or deoxyribonucleotide monomers connected together or linked by at least one 5' to 3' internucleotide linkage.

In some embodiments of the invention, the oligonucleotides are modified. The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, phosphate esters, alkylphosphonothioates, phosphoramidates, carbamates, carbonates, phosphate triesters, acetamidate, 2-0-methyls, and carboxymethyl esters. In one preferred embodiment of the invention, the oligonucleotide comprises at least one phosphorothioate linkage. The term "modified oligonucleotide" also encompasses oligonucleotides with a modified base and/or sugar. For example, a 3', 5'-substituted oligonucleotide is a modified oligonucleotide having sugars, at both its most 3' and 5' positions, are attached to a chemical group other than a hydroxyl group (at its 3' position) and other than a phosphate group (at its 5' position). Such modified oligonucleotide may also be referred to as a capped species. In addition, unoxidized or partially oxidized oligonucleotides having a substitution in one nonbridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention.

The portion of the MDR-1 gene to which the oligonucleotides of the invention are complementary includes any contiguous portion of a nucleotide sequence encoding a nucleotide binding site on P170. In preferred embodiments, this nucleotide binding site is the NB-1 site. In other preferred embodiments, the nucleotide sequence of the nucleotide binding site consists of bases 1708–1729 or 3637–3658 (SEQ ID NO: 1) of the MDR-1 gene, and portions of transcripts corresponding thereto and encoded thereby. In other embodiments, the oligonucleotides of the invention are complementary to less than the entire region that encodes the nucleotide binding site. In preferred embodiments, the oligonucleotides are at least 6, and preferably 12 to 50 nucleotides in length. In most preferred embodiments, the oligonucleotides are 14 to 30 nucleotides in length. In some embodiments, oligonucleotides complementary to these regions have the nucleotides sequence set forth in the Sequence Listing as SEQ ID NOS: 1–7.

In another aspect of the invention a therapeutic formulation is provided which includes an oligonucleotide of the invention, and in some embodiments, a physiologically acceptable carrier.

The invention also provides methods employing the formulation or oligonucleotides of the invention. In one aspect, a method of preventing the induction of multidrug resistance in a cancer cell undergoing chemotherapy is provided which includes the step of treating the cell with an oligonucleotide of the invention either before or during drug therapy. Hybridization of the oligonucleotide to the MDR-1 DNA or RNA prevents the expression of P170, thereby inhibiting the development of drug resistance by enabling the accumulation of drug inside the cell.

In another aspect, a method of preventing the expression of P170 in a cell is provided comprising the step of treating the cell with an oligonucleotide of the invention.

In yet another aspect, a method of treating multidrug resistant cancer cells is provided. In this method, the oligonucleotide of claim 1 is administered to the cells, which are then treated with a chemotherapeutic drug. The oligonucleotide prevents the expression of the MDR-1 gene, thereby enabling the drug to accumulate inside the cells.

In another aspect, the invention provides a method of screening for chemotherapeutic agents. In this method an oligonucleotide of the invention is administered to the cells for a time sufficient to enable the oligonucleotide to hybridize to MDR-1 DNA or a transcript thereof. The cell is then treated with the therapeutic drug-to-be-tested, and cell death is detected, cell death being indicative of the sensitivity of the cell to the drug. Hybridization of the oligonucleotide to the MDR-1 DNA or RNA prevents the expression of P170, thereby enabling the accumulation of drug inside the cell for a time long enough to cause the cell's death.

In another aspect, the invention provides a method of determining whether a cancer cell exhibiting a multiple drug resistance phenotype has this phenotype by virtue of MDR-1 expression. In this aspect, multiple drug resistant cancer cells are treated ex vivo with one or more chemotherapeutic agents against which MDR-1 is known to provide resistance. Prior to such treatment these cells are pretreated with an oligonucleotide according to the invention or with an unrelated oligonucleotide. Those cells that lose the drug resistance upon treatment with the oligonucleotide according to the invention, but not upon pretreatment with the unrelated oligonucleotide, are deemed to be drug resistant via expression of the MDR-1 gene.

BRIEF DESCRIPTION OF THE DRAWINGS

The foregoing and other aspects of the present invention, the various features thereof, as well as the invention itself may be more fully understood from the following description, when read together with the accompanying drawings in which.

DETAILED DESCRIPTION OF THE PREFERRED EMBODIMENTS

The patent and scientific literature referred to herein establishes the knowledge that is available to those with skill in the art. The issued U.S. patents, allowed applications, and references cited herein are hereby incorporated by reference.

P170 is a plasma membrane glycoprotein that is responsible for multiple drug resistance in mammalian cells. This protein is part of a larger protein family whose members each contain nucleotide binding sites and are involved with the transport of various molecules across membranes. Cells that express P170 are resistant to the toxic effects of a large number of chemotherapeutic drugs including colchicine, anthracyclines, actinomycin D, vinca alkaloids, and epipodophyllotoxin, among others. These drugs enter the cell via passive diffusion through the plasma membrane and are pumped back out by P170.

Figure 1:
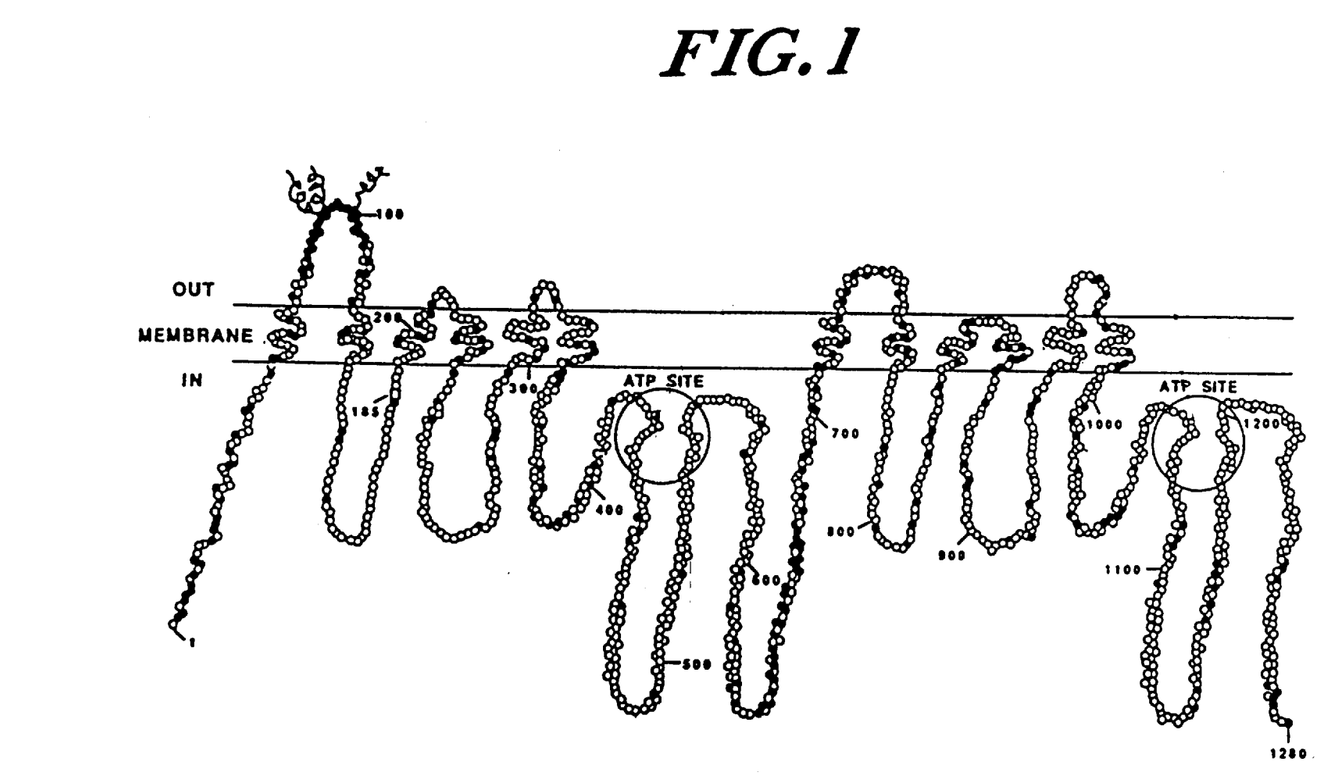
FIG. 1 is a schematic representation of the secondary structure of P170 and the regions of the amino acid sequence corresponding to the regions of the nucleotide sequence targeted by the oligonucleotides of the invention.

P170 is encoded by the MDR-1 gene. The human protein has 1280 amino acids and consists of two homologous halves joined by a linker region. Each half includes a nucleotide binding site whose amino acid sequences are highly homologous. P-170 and these duplicated nucleotide binding sites are shown schematically in FIG. 1.

The oligonucleotides of the invention are complementary to the nucleotide sequences which encode these nucleotide binding sites. The nucleotide sequences encoding these binding sites run from nucleotide 1708 through nucleotide 1729 and from nucleotide 3637 to nucleotide 3658 (see SEQ ID NO: 1) of the MDR-1 cDNA sequence ("A" of ATG start codon as number 1, Genebank accession number M14758). Some of the subject oligonucleotides are complementary to the entire sequence (i.e., to 1708–1729 and 3637–3658; SEQ ID NO: 1) and are at least 22 nucleotides in length. Alternatively, the oligonucleotides are complementary to less than an entire nucleotide-encoding site and thus include fewer than 22 nucleotides complementary thereto (e.g., SEQ ID NOS: 2–7. However, such oligonucleotides are complementary to any of at least six contiguous nucleotides within these two regions. Representative oligonucleotides of the invention are set forth below in TABLE 1.

as phosphoramidate, H-phosphonate chemistry, or methylphosphoramidate chemistry (see, e.g., Uhlmann et al. (1990) *Chem. Rev.* 90: 543–584; Agrawal et al. (1987) *Tetrahedron. Lett.* 28: (31): 3539–3542); Caruthers et al. (1987) *Meth. Enzymol.* 154: 287–313,; U.S. Pat. No. 5,149, 798) which can be carried out manually or by an automated synthesizer and then processed (reviewed in Agrawal et al. (1992) *Trends Biotechnol.* 10: 152–158).

The oligonucleotides of the invention may also be modified in a number of ways without compromising their ability to hybridize to MDR-1 DNA or mRNA. For example, the oligonucleotides may contains other than phosphodiester internucleotide linkages between the 5' end of one nucleotide and the 3' end of another nucleotide in which the 5' nucleotide phosphate has been replaced with any number of chemical groups. For example, oligonucleotides with phosphorothioate linkages can be prepared using methods well known in the field such as methoxyphosphoramidite (see, e.g., Agrawal et al. (1988) *Proc. Natl. Acad. Sci.* (USA) 85: 7079–7083) or H-phosphonate (see, e.g., Froehler (1986) *Tetrahedron Lett.* 27: 5575– 5578) chemistry. The synthetic methods described in Bergot et al. (*J. Chromatog.* (1992) 559: 35–42) can also be used. Examples of other chemical groups include alkylphosphonates, carbamates, phosphorodithioates, alkylphosphonothioates, phosphoramidates, phosphoramidites, phosphate esters, 2-0-methylribonucleosides, acetamidate, carboxymethyl esters, carbonates, and phosphate triesters. oligonucleotides with these linkages or other modifications can be prepared according to known methods (see, e.g., Agrawal and Goodchild (*Tetrahedron Lett.* (1987) 28: 3539–3542); Agrawal et al. (*Proc. Natl. Acad. Sci.* (USA) (1988) 85: 7079–7083); Uhlmann et al. *Chem. Rev.* (1990) 90: 534–583; and Agrawal et al. (*Trends Biotechnol.* (1992) 10: 152–158).

Other modifications include those which are internal or are at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the viral genome. Examples of such modified oligonucleotides include oligonucleotides with a modified base and/or sugar such as arabinose instead of ribose, or a 3', 5'-substituted oligonucleotide having a sugar which, at both its 3' and 5' positions is attached to a chemical group other

TABLE 1

| NAME | ANTISENSE SEQUENCE | TARGET | SEQ ID NO: |
|---|---|---|---|
| | 3'                          5' | | |
| 707 | TGTGCTCTTCCCACAGCCACTG | 1708–1729; 3637–3658 | 1 |
| 1110 | TGTGCTCTTCCCACAGCCAC | 1708–1727; 3637–3656 | 2 |
| 1111 | GTGCTCTTCCCACAGCCACT | 1709–1729; 3638–3657 | 3 |
| 1112 | TGCTCTTCCCACAGCCACTG | 1710–1729; 3639–3658 | 4 |
| 1113 | TCTTCCCACAGCCAC | 1713–1727; 3642–3656 | 5 |
| 1114 | CTCTTCCCAC | 1712–1721; 3642–3656 | 6 |
| 1115 | CAGCCA | 1719–1724; 3648–3653 | 7 |

The oligonucleotides of the invention are composed of deoxyribonucleotides, ribonucleotides, or any combination thereof, with the 5' end of one nucleotide and the 3' end of another nucleotide being covalently linked, in some cases, via a phosphodiester internucleotide linkage. These oligonucleotides can be prepared by art recognized methods such than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule (reviewed in Agrawal et al. (1992) *Trends Biotechnol.* 10: 152–158).

The inhibition of MDR-1 gene expression will potentiate the intracellular delivery of any xenobiotic or natural product which may act as a substrate for the MDR-1 gene product, P-170. Thus, the oligonucleotides of the invention, for example, in the form of a therapeutic formulation, are useful in methods of treating cells where it is desirable that an administered drug gain entry and remain in a cell. Such a cell may be cancerous or precancerous, and such a drug may be any cytotoxin known in the field to kill or control the proliferation of cancer cells.

In the methods of the invention, the therapeutic formulation contains at least one oligonucleotide as described above, along with a physiologically acceptable carrier. Some therapeutic formulations contain more than one type of oligonucleotide of the invention.

As used herein, a "physiologically acceptable carrier" includes any and all solvents, dispersion media, coatings, antibacterial and antifungal agents, isotonic and absorption-delaying agents, and agents which improve oligonucleotide uptake, and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

To demonstrate improved antisense inhibition of MDR-1 gene expression by the oligonucleotides of the invention relative to the inhibition by sequences reported in the literature, a number of experiments were conducted with cells expressing the cloned human MDR-1 gene. The cells were incubated with non-coding, random sequence control oligonucleotides (designated "493"; SEQ ID NO: 9); with an oligonucleotide with a nucleotide sequence reported in the literature to have anti-MDR-1 activity (designated "474"; SEQ ID NO: 8) (see, e.g., Corrias et al. (1992) Anticancer Res. 12: 1431–1438); or with one of several oligonucleotides of the invention which are complementary to the nucleotide sequences encoding the nucleotide biding sites on P170 and designed to target both regions of the MDR-1 mRNA which encode the two nucleotide-binding regions of the gene product (designated "707," "1110," "1111," and "1112" (SEQ ID NOS: 1, 2, 3, and 4, respectively)). The sequences of these oligonucleotides are shown in TABLE 1 as well as the Sequence Listing. The experiments in which these oligonucleotides were tested are described below and in greater detail in the EXAMPLES.

Figure 2:
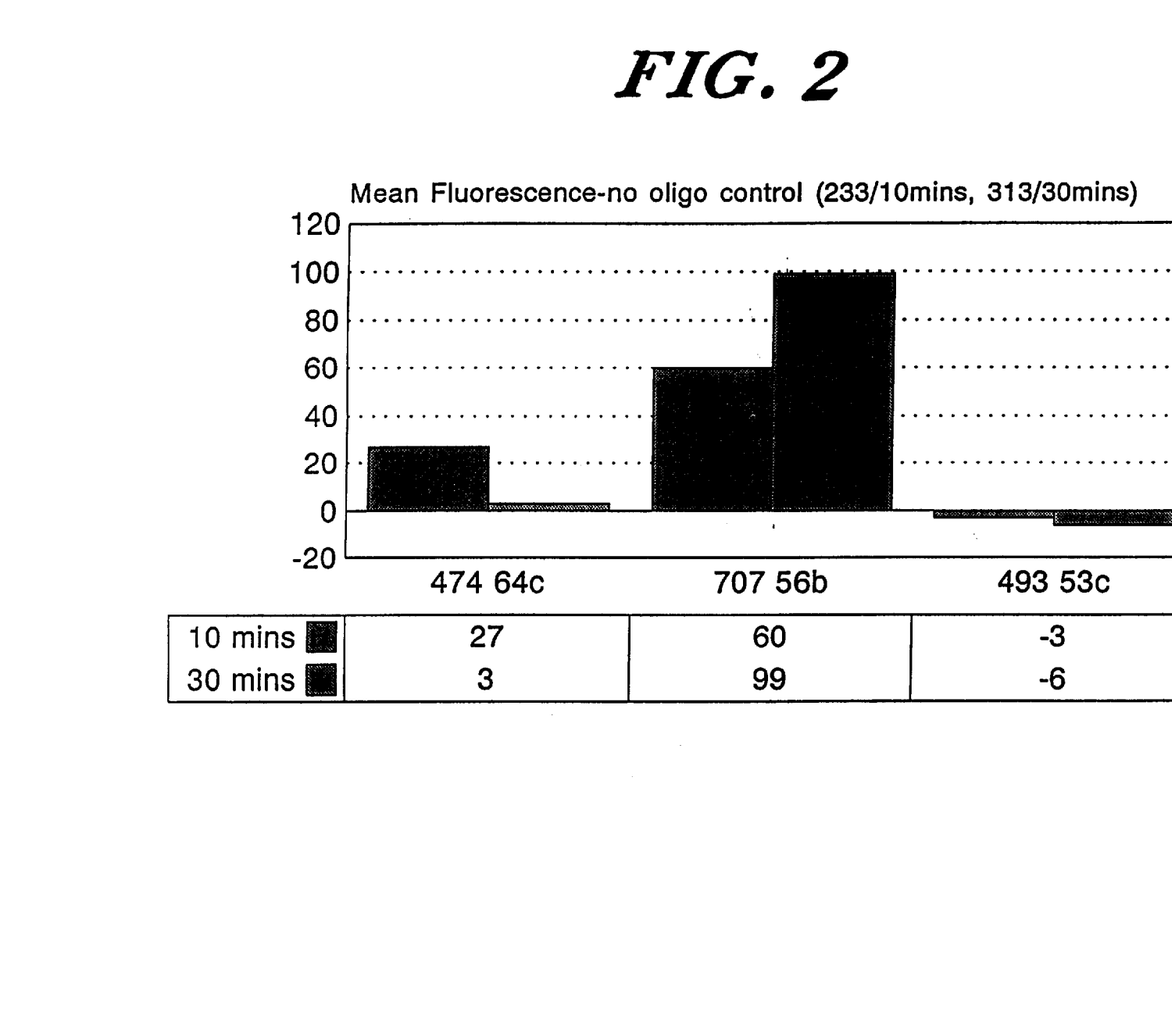
FIG. 2 is a graphic representation of the results of a rhodamine-123 uptake experiment performed on NIH 3T3-MDR cells treated with an oligonucleotide and lipofectamine, followed by rhodamine-123 for 10 or 30 minutes. The results are expressed as mean log fluorescence with the value of the "no oligonucleotide" control subtracted out.

That P170 in a cell culture used to test the nucleotides of the invention was a functioning pump which was able to remove certain drugs from the cytoplasm of the cell was assessed by measuring its ability to transport a known substrate such as rhodamine-123. The ability of cells to accumulate this fluorochrome is known to be inversely proportional to the level of MDR-1 expressed (Kessel et al. (1991) *Cancer Res.* 51: 4665–4670). Here, cells with high expression of the MDR-1 gene were obtained by inserting the human MDR-1 gene into NIH3T3 cells and selecting for cells stably expressing MDR-1 (Bruggemann et al. (1992) *J. Biolog. Chem.* 267: 21020–21026). These cells were used to examine the inhibition of rhodamine-123 accumulation in the cells treated with an oligonucleotide of the invention having SEQ ID NO: 1. FIG. 2 demonstrates the effects of this oligonucleotide in comparison with the results obtained with a published antisense oligonucleotide 474 (SEQ ID NO: 8) complementary to the 5' end of the MDR-1 transcript and a non-coding control oligonucleotide 493 (SEQ ID NO: 9). In this figure, the fluorescence obtained in non-treated cells has been subtracted to show more clearly the effects of the individual oligonucleotide treatments.

The control oligonucleotide had essentially no effect on rhodamine-123 accumulation. Cells treated with oligonucleotide 474 (SEQ ID NO: 6) had a minimal increase in rhodamine-123 accumulation after 10 minutes incubation, but were virtually no different from untreated control cells after 30 minutes incubation with rhodamine-123. In contrast, cells treated with an oligonucleotide of the invention (707, SEQ ID NO: 1) showed a large increase in rhodamine-123 accumulation after 10 minutes (about 26% over untreated controls) and after 30 minutes (about 31% over controls).

The transport of the chemotherapeutic drug daunorubicin (which is also fluorescent) was determined in cells in the presence and absence of verapamil, a small molecule inhibitor of the MDR-1 gene product. The difference between the level of fluorescence in verapamil and non-verapamil treated cells allows the determination of the residual level of P170 expressed in a given cells population.

Figure 3:
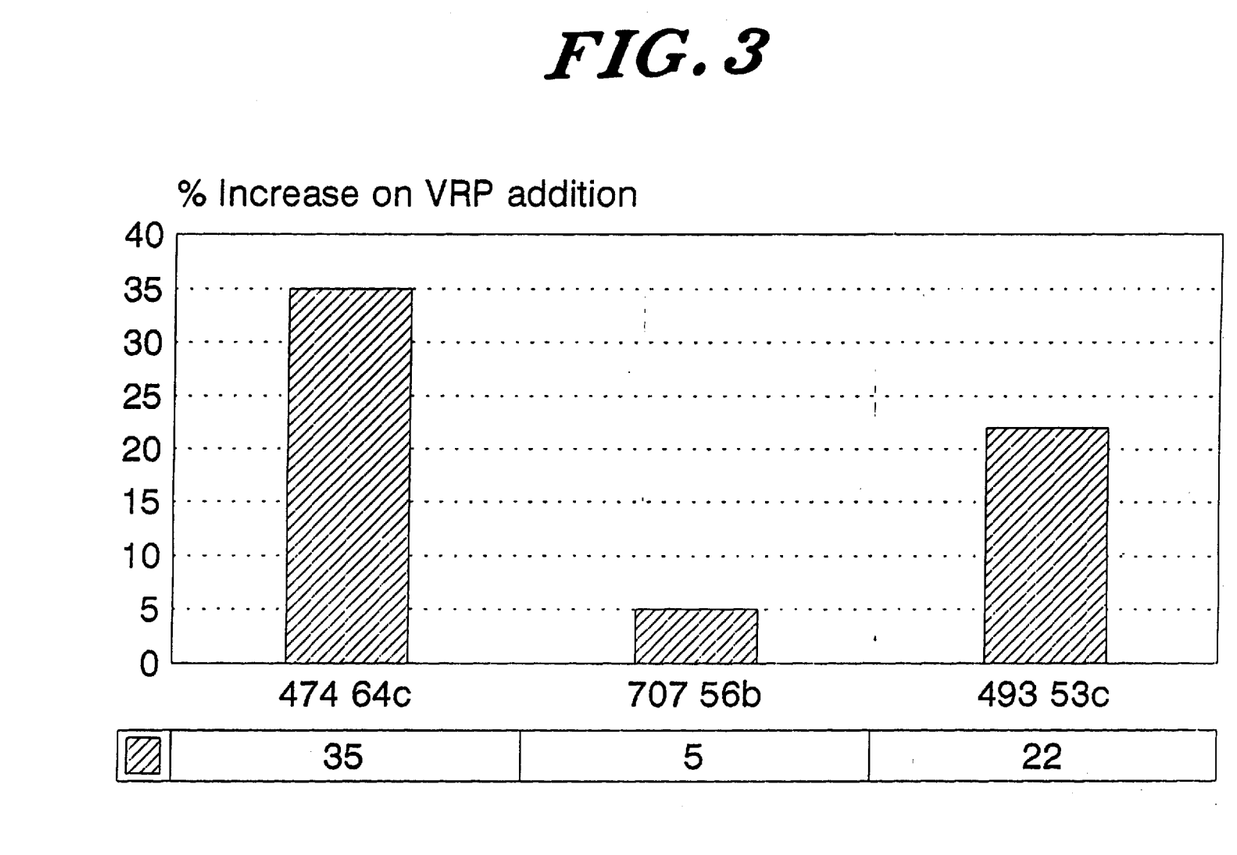
FIG. 3 is a graphic representation of the results of a daunorubicin uptake experiment performed on LoVo 350-1 cells treated with different oligonucleotides and lipofectamine, followed by daunorubicin or daunorubinicin and verapamil (control). The results are expressed as percent increase in mean fluorescence units as compared with the control.

The effect of verapamil on daunorubicin accumulation in control and antisense treated LoVo 350-1 cells is shown in FIG. 3. In cells co-incubated with verapamil and daunorubicin, there was a 22% increase in fluorescence in cells which had been pre-treated with the control oligonucleotide (SEQ ID NO: 9) and, surprisingly, a 35% increase in cells pre-treated with the 474 oligonucleotide (SEQ ID NO: 8). This indicates that there was a significant amount of P170 which was still expressed in these cells that could be inhibited by verapamil. In contrast, there was only a 5% increase in fluorescence by verapamil in cells which were pre-treated with an oligonucleotide (707) of the invention (SEQ ID NO: 1), indicating that this oligonucleotide had effectively blocked most of the MDR-1 expression.

Figure 4A:
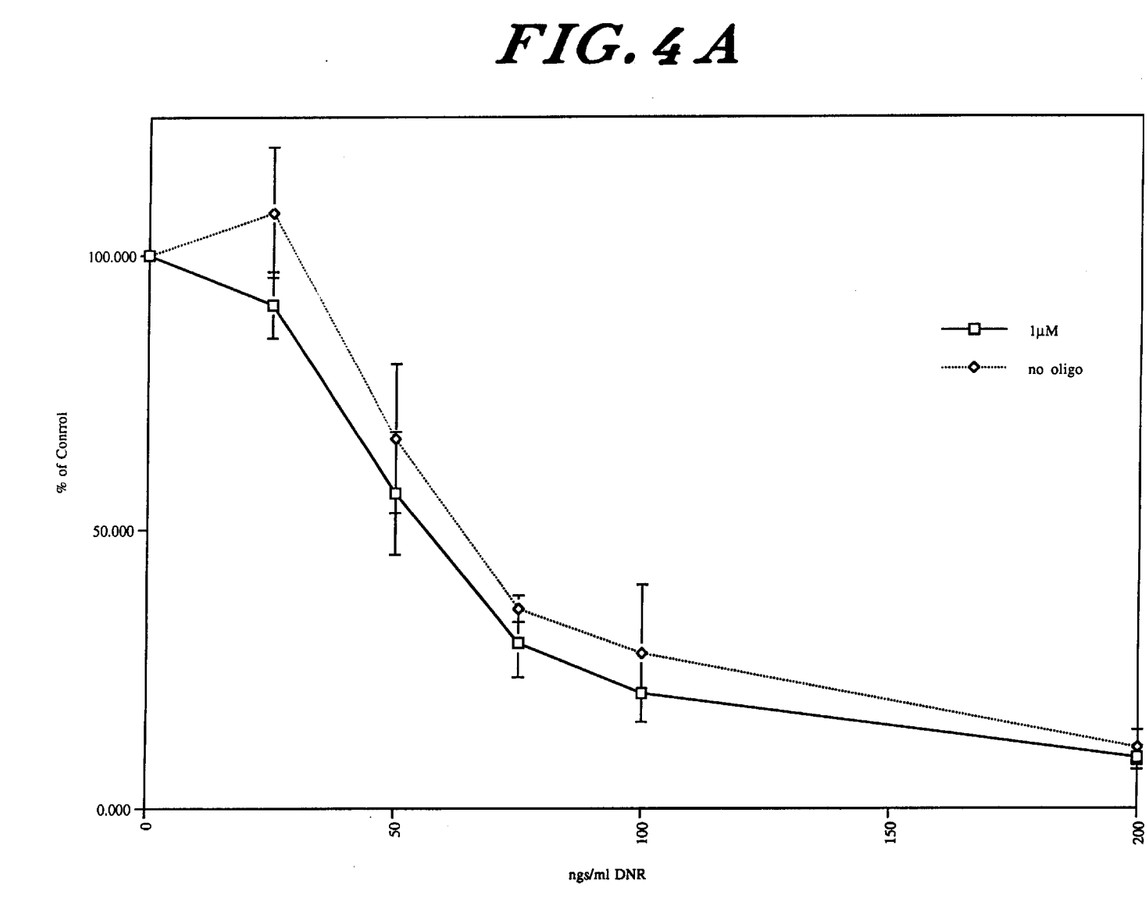
FIG. 4A is a graphic representation of the results of an MTT assay performed on LoVo 350-1 cells treated with the 493 oligonucleotide (SEQ ID NO: 9), followed by different concentrations of daunorubicin (DNR). The results are expressed as percent absorbance relative to control cells which had not been treated with oligonucleotide.
Figure 4B:
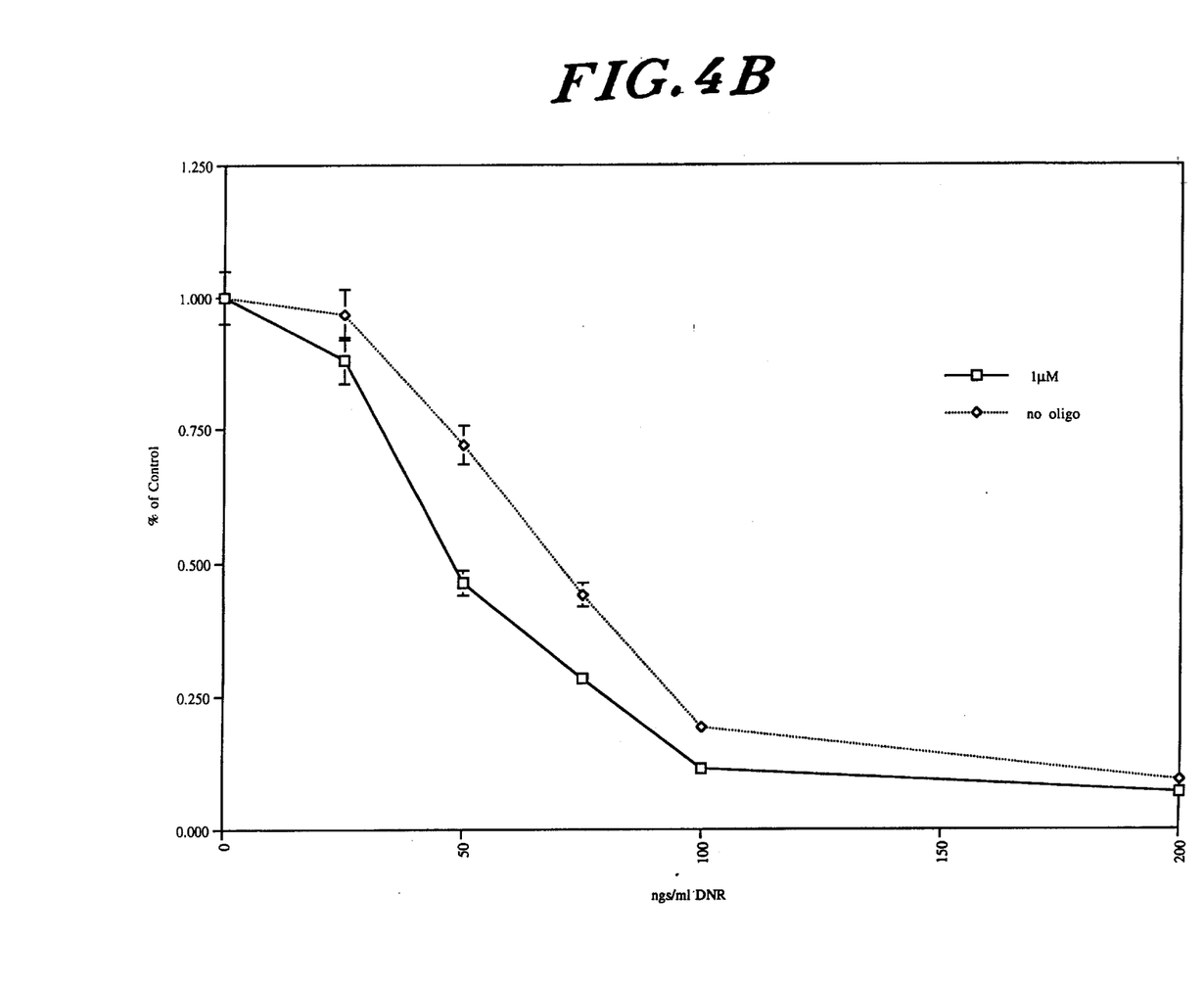
FIG. 4B is a graphic representation of the results of an MTT assay performed on LoVo 350-1 cells treated with the 474 oligonucleotide (SEQ ID NO: 9), followed by different concentrations of daunorubicin (DNR). The results are expressed as percent absorbance relative to control cells which had not been treated with oligonucleotide.
Figure 4C:
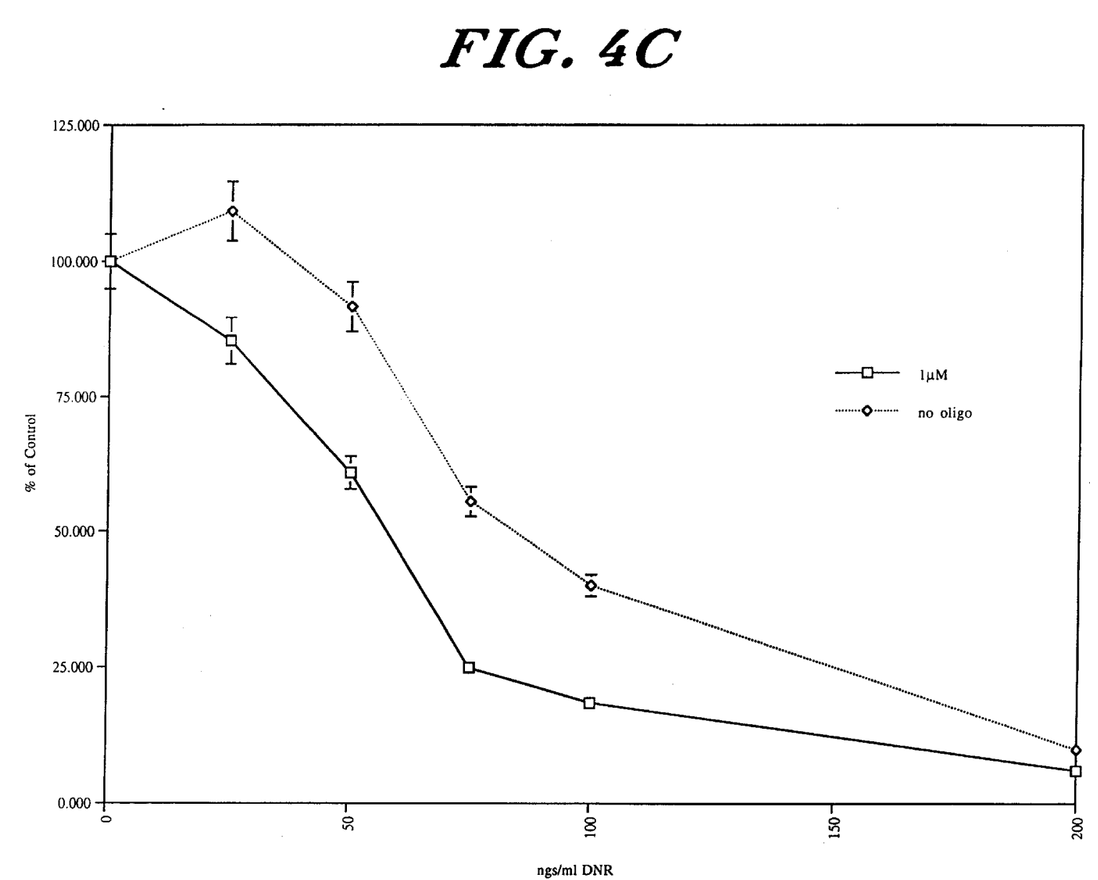
FIG. 4C is a graphic representation of the results of an MTT assay performed on LoVo 350-1 cells treated with an oligonucleotide of the invention (SEQ ID NO: 1), followed by different concentrations of daunorubicin (DNR). The results are expressed as percent absorbance relative to control cells which had not been treated with oligonucleotide.

The cytotoxicity of daunorubicin in oligonucleotide pre-treated and control cells was determined using the compound 3-(4,5,-dimethyl-thiazol-2-yl)-2,5-diphenyltetrazolium bromide (MTT) (Carmichael et al. (1987) *Cancer Res.* 47: 936–942). The results are shown in FIGS. 4A, 4B and 4C.

While there is a slight non-specific sensitization of cells to the cytotoxic effects of daunorubicin with the random sequence and some inhibition with the 474 oligonucleotide (SEQ ID NO: 8), there is a greater sensitization with an oligonucleotide of the invention (707, SEQ ID NO: 1). This is particularly apparent when comparing the total area between the survival curves for oligonucleotide treatment versus the no treatment controls.

The ability of oligonucleotides complementary to different portions of the nucleotide-binding sequence of MDR-1 to inhibit drug uptake by P170 was also compared. Cells were incubated with an oligonucleotide and then were exposed to rhodamine-123.

Figure 5:
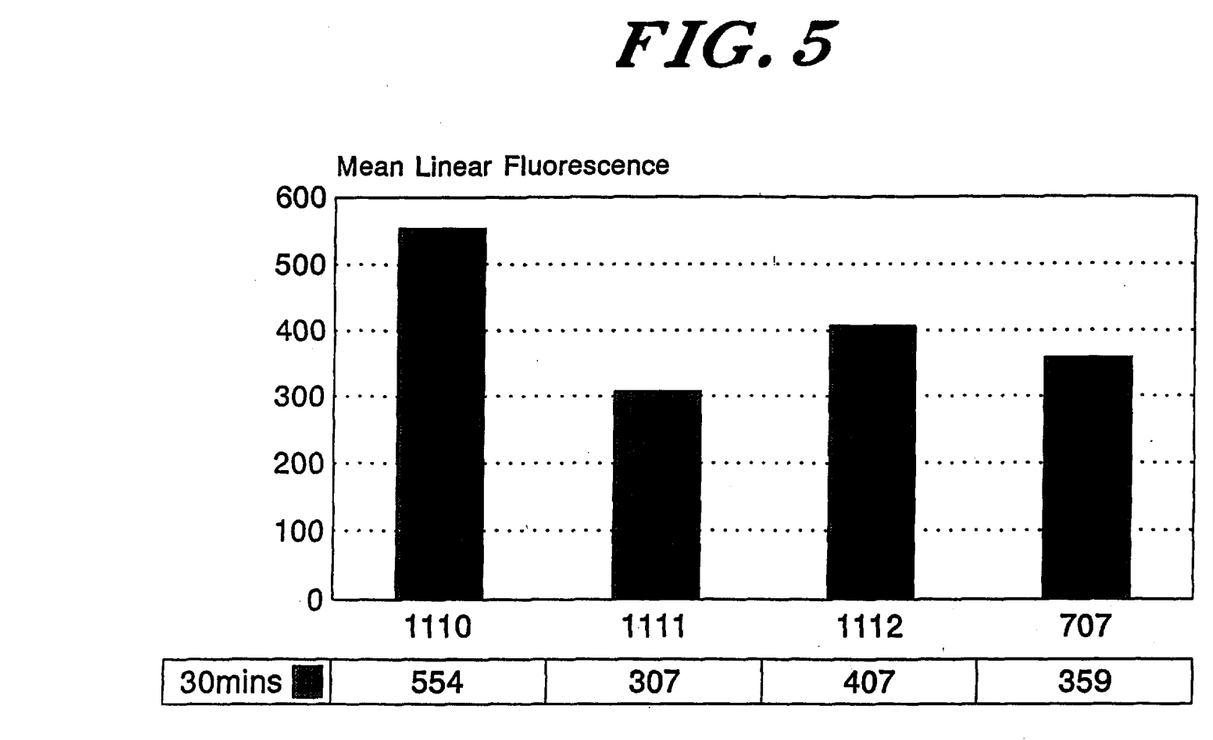
FIG. 5 is a graphic representation of the results of a rhodamine-123 uptake experiment performed on NIH 3T3-MDR cells treated with an oligonucleotide of the invention (707, 1110, 1111, 1112; SEQ ID NOS: 1–4, or with the 474 oligonucleotide (SEQ ID NO: 8), the 493 random oligonucleotide (SEQ ID NO: 9), or with no oligonucleotide, followed by rhodamine-123. The results are expressed as mean log fluorescence values.

The results in FIG. 5 demonstrate that oligonucleotides 707, 1110, 1111, and 1112 were able to restore some accumulation of rhodamine-123, indicating their ability to inhibit P170 expression. All showed enhanced accumulation of rhodamine-123 over 474 (SEQ ID NO: 8) (SEQ. ID. NO: 9) with oligonucleotide 1110 (SEQ ID NO: 2) approaching the parental NIH3T3.

The following examples illustrate the preferred modes of making and practicing the present invention, but are not meant to limit the scope of the invention since alternative methods may be utilized to obtain similar results.

EXAMPLES

1. Multidrug Resistant Cells

NIH3T3 cells expressing the human MDR-1 gene (NIH3T3-MDR) (Bruggemann et al. (1992) *J. Biolog. Chem.* 267: 21020–21026) were cultured in DMEM (4.5 g/l glucose) (Mediatech, Washington, D.C.), supplemented with 10% fetal bovine serum. Cells were passed into HyQ CCM2 serum-free medium (Hyclone, Logan, UT) immediately prior to treatment with antisense.

In other experiments, a drug-resistant human colon cancer cell line (LoVo 350-1) was used. This line was generated by treating parental LoVo cells (ATCC No. CCL 229, American Type Culture Collection, Rockville, Md.) grown in Ham's F12 medium (Mediatech, Herndon, Va.) with increasing doses of the chemotherapeutic drug daunorubicin (DNR) (Sigma, St. Louis, Mo.) over a period of several months. This treatment regimen has been shown to result in cells with high expression of MDR-1 (Grandi et al. (1986) *Br. J. Cancer* 54: 515–518). The cells were designated "LoVo 350-1" because they were exposed to concentrations of daunorubicin up to 350 ng/ml. All cells were grown in a humidified atmosphere of 5% $CO_2$. LoVo 350.1 cells were cultured in Ham's F12 media (Mediatech, Herndon, Va.) supplemented with 10% fetal bovine serum, and cytotoxicity experiments were performed in this medium. For daunorubicin uptake experiments, cells were passed into HyQ CCM2 serum-free medium (Hyclone) immediately prior to treatment with antisense.

2. Oligonucleotides

Phosphorothioate oligonucleotides ranging in size from 6 to 50 nucleotides were synthesized using a Millipore Model 8800 DNA synthesizer (Bedford, Mass.) using beta-cyanoethyl phosphoramidite chemistry and 3H-1,2-benzodithiol-3-one 1,1-dioxide (Beaucage; R.I. Chemical, Orange, Calif.). Alternatively, phosphodiester-linked oligonucleotides having different lengths are prepared using H-phosphonate chemistry as described in Uhlmann et al. (*Chem. Rev.* (1990) 90: 534–583). These oligonucleotides are listed in TABLE 1, above.

These same oligonucleotides are also prepared with at least one nonphosphodiester internucleotide linkage including a phosphorothioate, phosphorodithioate, phosphoramidate, alkylphosphonate, carbamate, and alkylphosphorothioate linkages at selected positions using the procedures described in Uhlmann et al. *(Chem. Rev.* (1990) 90: 534–583).

3. Rhodamine-123 Transport #1

HyQ CCM2-media was removed from a subconfluent 100 mm petri dish culture of NIH3T3-MDR cells and oligonucleotides at a concentration of 0.5 $\mu$M were added with 2.5 $\mu$g/ml lipofectamine (Gibco BRL, Gaithersburg, Md.) in a final volume of 6 ml HyQ CCM2 for 7 hours. The media was then replaced with fresh media containing a final concentration of 0.5 $\mu$M oligonucleotide for a total of 88 hours. An additional 2 ml of media containing 0.5 $\mu$M of oligonucleotide was added at 40 hours. Prior to analysis of rhodamine-123 uptake, the media was aspirated and the cells washed twice with warm phosphate buffered saline (PBS). Rhodamine-123 at a final concentration of 20 $\mu$g/ml in HyQ CCM2 was added and the plates incubated at 37° C. for 10 mins or 30 mins to allow the influx to occur. The cells are then prepared as rapidly as possible for flow cytometry analysis by washing with cold PBS, trypsinized, and collected in Ham's F12 media and analyzed for rhodamine-123 associated fluorescence using a Coulter Epics XL Flow Cytometer and Coulter Software version 1.5 (Coulter, Hialeah, Fla.). Rhodamine 123 fluorescence was measured using and excitation at 488 nm with a 525 nm band pass filter. All reagents used post influx contained 10 $\mu$M verapamil (Sigma) to stop the pump action. The results are shown in FIG. 3. Values given are mean log fluorescence values subtracting out the "no oligonucleotide" control.

4. Rhodamine-123 Transport- #2

70,000 cells were seeded into 100 mM petri dishes (Costar, Cambridge, Mass. 02140)t in DMEM, 4.6 g glucose, supplemented with 10% fetal bovine serum, and allowed to attach for 6 hours. Oligonucleotides 707, 1110, 1111, and 1112 (SEQ ID NOS: 1–4, respectively) at a final concentration of 2 $\mu$M were added to a final volume of 7 ml DMEM. An additional 2 ml media containing 2 $\mu$M of oligonucleotides were added at 64 hours.

After approximately 88 hours, the following R-123 assay was performed. The media was aspirated and the cells washed twice with warm PBS+$Ca^{3+}$ and $Mg^{2+}$. R-123 at a concentration of 20 $\mu$g/ml in DMEM was added and the plates incubated at 37° C. in 5% $CO_2$ for 30 mins to allow the influx to occur. The cells were then prepared as rapidly as possible for flow cytometry analysis by washing with cold PBS without $Ca^{2+}$ and $Mg^{2+}$, trypsinized, collected in DMEM media, and analyzed on a flow cytometer (Coulter Epics Excel, Hialeah, Fla.). All reagents used post influx contained 10 $\mu$M verapamil to stop the pump action. The results are shown in FIG. 5.

5. Daunorubicin Transport 160,000 cells were seeded into 100 mM dishes (Costar, Cambridge, Mass.) in Ham's F12 media supplemented with 10% fetal bovine serum, and allowed to attach overnight. The media was removed and oligonucleotides at a concentration of 0.5 $\mu$M and lipofectamine (Gibco BRL, Gaitherburg, Md.) at 2.5 $\mu$g/ml in a final volume of 6 ml HyQ CCM2 serum free media were added for 6.5 hours. The media was then replaced with fresh media containing a final concentration of 0.5 $\mu$M oligonucleotide for a total of 72 hours. An additional 2 mls of media containing 0.5 $\mu$M of oligonucleotide was added at 48 hours.

To determine daunorubicin uptake the media was aspirated after oligonucleotide treatment and the cells washed twice with PBS. Cells were then trypsinized and resuspended in 2 ml Ham's F12 media supplemented with 10% FBS and split into two aliquots. Each received a final concentration of 4 $\mu$g/ml daunorubicin; one aliquot also received verapamil (60 nM). The cells were then incubated at 37° C. for 30 mins. Flow cytometry was subsequently performed using the Coulter Epics X-L Flow Cytometer with an excitation of 488 nm and a 620 nm band pass filter. Values given are expressed as percent increase in mean fluorescence units on addition of the inhibitor, verapamil. The results are shown in FIG. 4.

6. Daunorubicin Cytotoxicity with LoVo 350-1 Cells

Cells were seeded at 150 cells/well in 200 $\mu$l of complete medium in a 96 well plate. A day after seeding, the media was aspirated and 100 μl complete medium containing 1 μM oligonucleotide was added. The following day another 100 1 μl of complete medium containing 1 μM oligonucleotide was added. The next day the medium was changed to remove oligonucleotide and daunorubicin (0 to 200 ng/ml) was added for 24 hours.

Five days later the viability of cells was determined by the MTT method. Briefly, to each well of the 96-well plate, 50 1 μl of a 2 mg/ml stock of MTT (Sigma) made up in PBS and filter sterilized was added. The plates were then incubated for 2 hours at 37° C. The media was then aspirated being careful to avoid any crystals that had formed. 100 1 μl DMSO was then added to solubilize the blue formazan product. The absorbance was read on a Ceres 900HDi plate reader (Biotek Instruments Inc., Winooski, Vt.) at 570 nm subtracting out 620 nm for background. The results are shown in FIGS. 4A, 4B, and 4C. The data are expressed as percent absorbance relative to cells which were not treated with daunorubicin.

7. In Vivo Studies

To assess the ability of antisense oligonucleotides to reverse drug resistance in an in vivo situation, the following studies are done. Human tumor cell lines are used to generate tumors in the nude mouse model. These lines include the following drug resistant cells lines: LoVo 350-1, HCT200-1, drug-resistant CCRF-CEM, NCI-H596 and NCI-H446 cells.

Subconfluent cells cultured at 37° C. under 5% humidified $CO_2$ C are treated with an antisense or control oligonucleotides at 0.5 to 3 μM for four days. At the end of this time, 1 to 10 million cells are harvested and injected subcutaneously or intraperitoneally into groups of 20 nude mice to form tumors. Group 1 consists of control animals receiving only untreated tumor cells and solvent control the following day; group 2 consists of animals receiving untreated tumor cells and the following day receiving a dose of chemotherapeutic agent shown to give a marginal anti-tumor effect; group 3 consists of animals receiving tumor cells pre-treated with 0.5 μM antisense and the following day receiving the dose of chemotherapeutic agent used in group 2; group 4 includes animals receiving tumor cells pre-treated with 1 μM antisense oligonucleotide and the following day receiving the dose of the chemotherapeutic agent used in group 2; group 5 includes 20 animals receiving tumor cells pre-treated with 3 μM antisense oligonucleotide and the following day receiving the dose of chemotherapeutic agent used in group 2. This experiment is repeated with the control oligonucleotide. The following day, mice are treated with the highest tolerated dose of one of several different chemotherapeutic agents which are all substrates for the MDR-1 gene product: vincristine, taxol (Bio-Synthesis, Inc., Lewisville, Tex.) or daunorubicin. It has been shown that reduced MDR-1 levels persist for up to .U48 hours after antisense treatment (Corrias et al. (1992) *Antisense Res.* 12: 1431–1438). Tumorigenicity is scored either by animal survival, tumor size (for subcutaneous tumors), or tumor burden (as indicated by the number and/or size of tumors formed after intraperitoneal administration of tumor cells).

In the second type of experiment, mice are treated with oligonucleotides after tumor cell inoculation. Specifically, a day after inoculating tumor cells, mice are injected intraperitoneally with 60 mg/kg oligonucleotide on days 1, 2, 3 and 4. On day 5 after inoculating with tumor cells, animals receive a dose of chemotherapeutic agent shown to give a marginal anti-tumor effect. Antisense treated animals are compared with control oligonucleotide treated and untreated animals.

In other experiments, animals bearing tumors are treated with oligonucleotides, and the tumor removed and characterized for drug sensitivity in vitro. Specifically, tumor cells are inoculated into immune-deficient mice. After two weeks, when a tumor has formed, the mice are treated for four days with 60 mg/kg oligonucleotide. The tumor is then excised and sensitivity to chemotherapeutic agents determined by the fluorescent cytoprint method (Meitner (1991) *Oncology* 5: 75–88).

In addition, the effect of MDR-1 targeted antisense oligonucleotides on the development MDR-1-mediated drug resistance in vivo is determined as follows. Parental drug-sensitive cells such as LoVo and/or HCT15 are implanted into nude mice which are then treated with a low dose of chemotherapy in the presence and absence of oligonucleotides. The regimen of chemotherapy treatment chosen is such that tumor cells are not completely killed by the treatment but drug resistant cells are generated by the treatment (as occurs in the clinic). The ability of the antisense oligonucleotides of the invention to inhibit the formation of drug resistant tumor variants is then assessed.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. An oligonucleotide having a nucleotide sequence as set forth in SEQ ID NO: 1.

2. An oligonucleotide 1 having a nucleotide sequence as set forth in SEQ ID NO: 2.

3. An oligonucleotide having a nucleotide sequence as set forth in SEQ ID NO: 3.

4. An oligonucleotide having a nucleotide sequence as set forth in SEQ ID NO: 4.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO ( i v ) ANTI-SENSE: YES ( x i ) SEQUENCE DESCRIPTION: SEQ ID NO:1:

TGTGCTCTTC CCACAGCCAC TG                    22

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:2:

TGTGCTCTTC CCACAGCCAC                       20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:3:

GTGCTCTTCC CACAGCCACT                       20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:4:

TGCTCTTCCC ACAGCCACTG                       20

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:5:

TCTTCCCACA GCCAC                                                                                                  15

( 2 ) INFORMATION FOR SEQ ID NO:6:

( i ) SEQUENCE CHARACTERISTICS:
          ( A ) LENGTH: 10 base pairs
          ( B ) TYPE: nucleic acid
          ( C ) STRANDEDNESS: single
          ( D ) TOPOLOGY: linear      ( i i ) MOLECULE TYPE: cDNA     ( i i i ) HYPOTHETICAL: NO      ( i v ) ANTI-SENSE: YES       ( x i ) SEQUENCE DESCRIPTION: SEQ ID NO:6:

CTCTTCCCAC                                                                                                        10

( 2 ) INFORMATION FOR SEQ ID NO:7:

( i ) SEQUENCE CHARACTERISTICS:
          ( A ) LENGTH: 6 base pairs
          ( B ) TYPE: nucleic acid
          ( C ) STRANDEDNESS: single
          ( D ) TOPOLOGY: linear      ( i i ) MOLECULE TYPE: cDNA     ( i i i ) HYPOTHETICAL: NO      ( i v ) ANTI-SENSE: YES       ( x i ) SEQUENCE DESCRIPTION: SEQ ID NO:7:

CAGCCA                                                                                                            6

( 2 ) INFORMATION FOR SEQ ID NO:8:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear      ( i i ) MOLECULE TYPE: cDNA     ( i i i ) HYPOTHETICAL: NO      ( i v ) ANTI-SENSE: YES       ( x i ) SEQUENCE DESCRIPTION: SEQ ID NO:8:

CCCGACCTCG CGCTCCTTGG                                                                                             20

( 2 ) INFORMATION FOR SEQ ID NO:9:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear      ( i i ) MOLECULE TYPE: cDNA     ( i i i ) HYPOTHETICAL: NO      ( i v ) ANTI-SENSE: YES       ( x i ) SEQUENCE DESCRIPTION: SEQ ID NO:9:

CTGACTGCCA ACTATGAACA                                                                                             20